(12) United States Patent
Lee-Chen et al.

(10) Patent No.: US 9,795,600 B2
(45) Date of Patent: Oct. 24, 2017

(54) METHOD FOR TREATING ABNORMAL β-AMYLOID MEDIATED DISEASES

(71) Applicant: NATIONAL TAIWAN NORMAL UNIVERSITY, Taipei (TW)

(72) Inventors: Guey-Jen Lee-Chen, Taipei (TW); Hsiu-Mei Hsieh, Taipei (TW); Ching-Fa Yao, Taipei (TW)

(73) Assignee: NATIONAL TAIWAN NORMAL UNIVERSITY, Taipei (TW)

( * ) Notice: Subject to any disclaimer, the term of this patent is extended or adjusted under 35 U.S.C. 154(b) by 0 days.

(21) Appl. No.: 14/709,968

(22) Filed: May 12, 2015

(65) Prior Publication Data

US 2016/0143899 A1    May 26, 2016

(30) Foreign Application Priority Data

Nov. 25, 2014 (TW) .............................. 103140763 A

(51) Int. Cl.
| | |
|---|---|
| *A61K 31/40* | (2006.01) |
| *A61K 31/405* | (2006.01) |
| *A61K 31/4709* | (2006.01) |
| *A61K 31/404* | (2006.01) |
| *A61K 31/00* | (2006.01) |

(52) U.S. Cl.
CPC .......... *A61K 31/4709* (2013.01); *A61K 31/00* (2013.01); *A61K 31/404* (2013.01)

(58) Field of Classification Search
None
See application file for complete search history.

(56) References Cited

FOREIGN PATENT DOCUMENTS

CN    104109125    * 10/2014

OTHER PUBLICATIONS

Chintakunta et al., JOC, 2012, 77, 8451-8464.*
Hopkins, ACS. Chem. Neurosci. 2011, 2, 279-280.*
Chiu YJ, Lin CH, Huang CH, Lin TH, Lee CM, Yao CF and, Lee-Chen Guey-Jen,The Potential of Synthetic Indolylquinoline Derivatives for AB Aggregation Reduction by the Enhancement of Small Chaperone Protein and Apolipoprotein E, Department of life Science, National Taiwan Normal University, Taipei, Taiwan, pp. 36, Dec. 1-2, 2014.
Ya-Jen Chiu, Chen-Hsiang Huang, Chi-Mei Lee, Chih-Hsin Lin, Te-Hsien Lin,Guey-Jen Lee-Chen, The potential of synthetic indolylquinoline derivatives for Aβ aggregation reduction by enhancement of APOE, CHAT and HSPB1, Department of life Science, National Taiwan Normal University, p. 288, Mar. 21-22, 2015.

* cited by examiner

*Primary Examiner* — Shobha Kantamneni
(74) *Attorney, Agent, or Firm* — Bacon & Thomas, PLLC

(57) ABSTRACT

A method for treating abnormal β-amyloid mediated diseases is disclosed, comprising administering a pharmaceutical composition to a subject in need, wherein the pharmaceutical composition comprises an indolylquinoline derivative represented by the following formula 1:

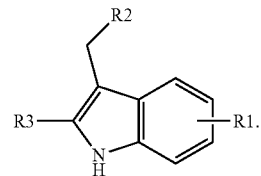

4 Claims, 5 Drawing Sheets

Compound 1 $C_{19}H_{16}N_2O_3$

Compound 6 $C_{21}H_{20}N_2O_3$

Compound 2 $C_{20}H_{18}N_2O_3$

Compound 7 $C_{19}H_{16}N_2$

Compound 3 $C_{25}H_{20}N_2O_3$

Compound 8 $C_{20}H_{25}N_2$

Compound 9 $C_{19}H_{15}BrN_2$

Compound 4 $C_{19}H_{15}BrN_2O_3$

Compound 10 $C_{21}H_{20}N_2$

Compound 5 $C_{20}H_{18}N_2O_4$

Compound 11 $C_{21}H_{18}N_2O_5$

METHOD FOR TREATING ABNORMAL β-AMYLOID MEDIATED DISEASES

CROSS REFERENCE TO RELATED APPLICATION

This application claims the benefits of the Taiwan Patent Application Serial Number 103140763, filed on Nov. 25, 2014, the subject matter of which is incorporated herein by reference.

BACKGROUND OF THE INVENTION

1. Field of the Invention

The present invention relates to a method for treating abnormal β-amyloid mediated diseases with a pharmaceutical composition, wherein a compound contained in the pharmaceutical composition is served as a chemical chaperone and enhances heat shock protein HSPB1 activity to facilitate the β-amyloid folding; therefore, the purposes of inhibiting β-amyloid aggregation, decreasing reactive oxygen species level in cells, and promoting neurite outgrowth can be achieved.

2. Description of Related Art

Alzheimer's disease (AD) is the most prevalent form of dementia in elderly patients causing neurodegeneration. The progressive cognitive decline and memory loss are usually observed in AD patients, and health expenditures and costs of care are high and expensive for AD patients. Significant neurological symptoms are not observed in the early stage of AD, and can be revealed in the middle and late stages thereof. The most observed symptoms are extrapyramidal symptoms, including increased muscle tone, and increased deep tendon reflex or myoclonus. Sometimes, epilepsy may also occur.

Although the drugs used nowadays cannot completely cure AD, some drugs are proved having efficacy of improving cognitive impairment. Currently, two kinds of drugs have been proved by the U.S. Food and Drug Administration, one is cholinesterase inhibitors including rivastigmine, donepezil and galantamine, and the other one is N-methyl-D-aspartate (NMDA) receptor antagonist such as memantine. Except for the administration of drugs for improving cognitive impairment, other suitable drugs also have to be administered to AD patients with other symptoms derived from AD such as depression and sleeplessness.

The worldwide populations with AD are gradually increased. Therefore, it is desirable to provide a method or a pharmaceutical composition for treating β-amyloid mediated diseases, which can be used to treat neurodegenerative diseases such as AD to further delay disease progression and improve patients' quality of life.

SUMMARY OF THE INVENTION

The object of the present invention is to provide a pharmaceutical composition for treating β-amyloid mediated diseases, to treat neurodegenerative diseases such as Alzheimer's disease.

Another object of the present invention is to provide a method for treating β-amyloid mediated diseases with the pharmaceutical composition of the present invention.

Another object of the present invention is to provide a use of the pharmaceutical composition of the present invention for manufacturing a drug of β-amyloid mediated diseases.

In addition, another object of the present invention is to provide a pharmaceutical composition for inhibiting β-amyloid aggregation, wherein the active component contained therein can be served as chemical chaperone or activate chaperone activity to inhibit β-amyloid aggregation and decrease reactive oxygen species (ROS) level.

Another object of the present invention is to provide a method for inhibiting β-amyloid aggregation in a subject with the pharmaceutical composition of the present invention.

A further another object of the present invention is to provide a use of the pharmaceutical composition of the present invention for manufacturing a drug for inhibiting β-amyloid aggregation.

To achieve the object, the pharmaceutical composition of the present invention comprises: a compound represented by the following formula 1,

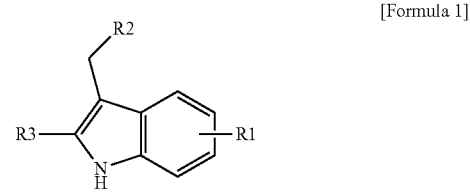

[Formula 1]

wherein R1 and R3 are independently H or an alkyl group, in which the alkyl group is a $C_1$-$C_{10}$ linear or branched monovalent hydrocarbon group; and R2 is

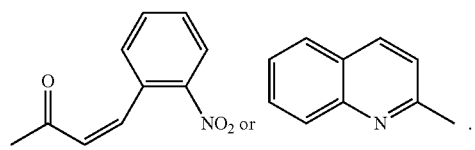

In addition, the method for treating an abnormal β-amyloid mediated diseases of the present invention comprises: administering the aforementioned pharmaceutical composition to a subject in need. Furthermore, the method for inhibiting β-amyloid aggregation in a subject of the present invention comprises: administering the aforementioned pharmaceutical composition to a subject.

In the present invention, the term "alkyl group" refers to a $C_1$-$C_{10}$ linear or branched monovalent hydrocarbon group; and the examples thereof comprise, but not limited to, methyl, ethyl, n-propyl, iso-propyl, n-butyl, iso-butyl and tert-butyl.

In the present invention, the compound represented by the formula 1 preferably is a compound represented by the following formulas 2 to 5:

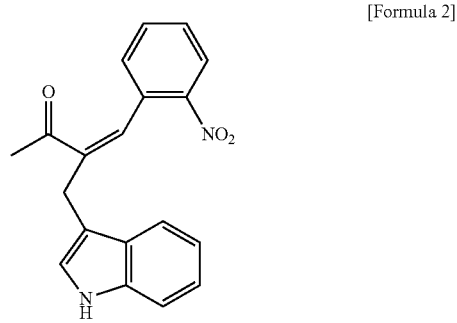

[Formula 2]

[Formula 3]

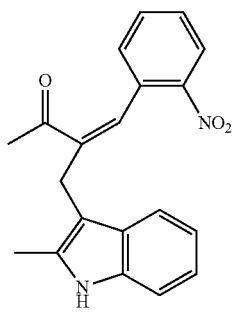

[Formula 4]

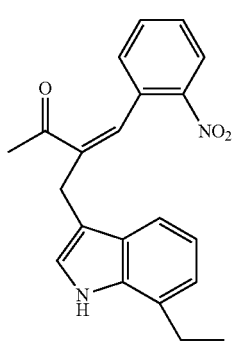

[Formula 5]

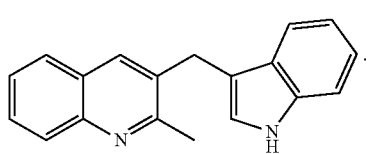

The pharmaceutical composition of the present invention may comprise one or more compounds represented by the formula 1. For example, the pharmaceutical composition of the present invention may comprise one or more compounds selected from the group consisting of compounds represented by the formulas 2 to 5.

In the pharmaceutical composition of the present invention, the compound contained therein itself has chemical chaperone activity or activates chaperone activity, to achieve the purpose of inhibiting β-amyloid aggregation and decreasing reactive oxygen species (ROS) level. Herein, in the chaperone pathway, the activity of heat shock 27 kDa protein 1 (HSPB1) can be enhanced, and the present invention is not limited thereto.

Abnormal protein aggregations are usually observed in brains of patients having neurodegenerative disorders. Among the known neurodegenerative disorders, Alzheimer's disease (AD) is the most prevalent form of dementia associated with progressive cognitive decline and memory loss. Extracellular β-amyloid (Aβ) is a major constituent of senile plaques, one of the hallmarks of AD. Aβ deposition causes neuronal death via a number of possible mechanisms including oxidative stress (increased ROS level). As Aβ aggregates show good correlation with neurotoxic effect, therapeutic approaches to identify novel Aβ aggregate reducers will be effective for the disease treatment. In addition, chaperone can identify and inhibit abnormal protein aggregation to protect neurons.

Herein, the types of the abnormal β-amyloid mediated disease of the present invention are not particularly limited, and can be Alzheimer's disease.

In the pharmaceutical composition of the present invention, the concentration of the compound of the formula 1 is not particularly limited, and can be adjusted according to disorder severity or complementary medicines. In one example of the present invention, the concentration of the compound of the formula 1 is in a range from 1 μM to 50 μM, and preferably from 1 μM to 30 μM, based on a total weight of the pharmaceutical composition. The pharmaceutical composition may further comprise: at least one pharmaceutically acceptable carrier, a diluent, or an excipient. For example, the compound can be encapsulated into liposome to facilitate delivery and absorption. Alternatively, the compound can be diluted with aqueous suspension, dispersion or solution to facilitate injection. Or, the compound can be prepared in a form of a capsule or tablet for storage and carrying. In addition, an effective concentration of the compound of the formula 1 may be changed according to administration, use of excipient, or co-use with other active agents; and a person skilled in the art can adjust the concentration of the compound of the formula 1 in the pharmaceutical composition or the dose of the pharmaceutical composition to achieve the purpose of obtaining desired curative effect.

More specifically, the compound of the formula 1 of the present invention can be formulated in a solid or liquid form. The solid formulation form may include, but is not limited to, powders, granules, tablets, capsules and suppositories. The solid formulation may comprise, but is not limited to, excipients, flavoring agents, binders, preservatives, disintegrants, glidants and fillers. The liquid formation form may include, but is not limited to, water, solutions such as propylene glycol solution, suspensions and emulsions, which may be prepared by mixing with suitable coloring agents, flavoring agents, stabilizers and viscosity-increasing agent.

For example, a powder formulation may be prepared by simply mixing the compound of the formula 1 of the present invention with suitable pharmaceutically acceptable excipients such as sucrose, starch and microcrystalline cellulose. A granule formulation may be prepared by mixing the compound of the formula 1 of the present invention with suitable pharmaceutically acceptable excipients and/or suitable pharmaceutically acceptable binders such as polyvinyl pyrrolidone and hydroxypropyl cellulose, followed by wet granulation method using a solvent such as water, ethanol and isopropanol, or dry granulation method using compression force. Also, a tablet formulation may be prepared by mixing the granule formulation with suitable pharmaceutically acceptable glidants such as magnesium stearate, followed by tableting using a tablet machine. Hence, a person skilled in the art can appropriately choose suitable formulation according to his/her needs.

In the present invention, the term "treat" refer to the case that the pharmaceutical composition of the present invention is applied to a subject suffering from abnormal β-amyloid mediated disease such as Alzheimer's disease, having symptoms of disease, or having a tendency of development of disease, in order to achieve the mitigation, slowing, therapy, improvement, or recovery of the tendency of the disease and symptoms.

To implement the method according to the present invention, the above pharmaceutical composition can be administered via oral administering, parenteral administering, inhalation spray administering, topical administering, rectal administering, nasal administering, sublingual administering, vaginal administering, or implanted reservoir, and so on. The term "parenteral" used here refers to subcutaneous injection, intradermal injection, intravenous injection, intramuscular injection, intra-articular injection, intraarterial injection, joint fluid injection, intrathoracic injection, intrathecal injection, injection at morbid site, and intracranial injection or injection technique.

Other objects, advantages, and novel features of the invention will become more apparent from the following detailed description when taken in conjunction with the accompanying drawings.

DETAILED DESCRIPTION OF THE PREFERRED EMBODIMENT

[Indolylquinoline Derivatives]

Figure 1:
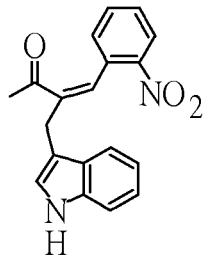
FIG. 1 shows chemical structures of 11 indolylquinoline derivatives used in examples of the present invention.
Figure 1:
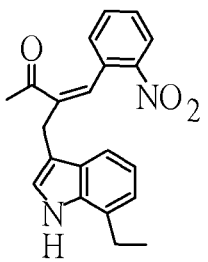
Figure 1:
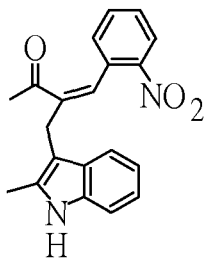
Figure 1:
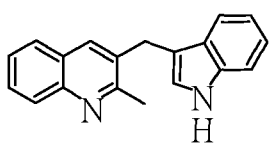
Figure 1:
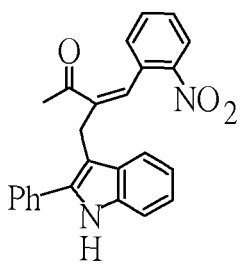
Figure 1:
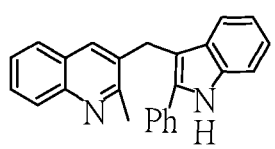
Figure 1:
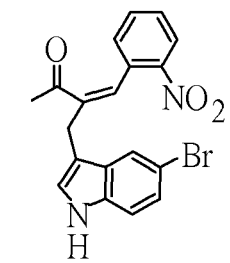
Figure 1:
Figure 1:
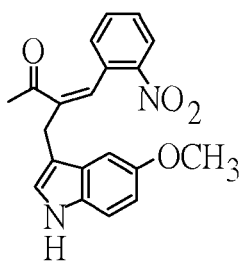
Figure 1:
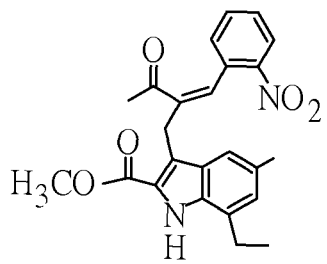

In the following examples, the used indolylquinoline derivatives are available from Prof. Ching-Fa Yao in National Taiwan Normal University. FIG. 1 shows 11 kinds of indolylquinoline derivatives used herein, which are named as compound 1 to compound 11.

[Trx-His-Aβ Biochemical Assay]

Figure 2:
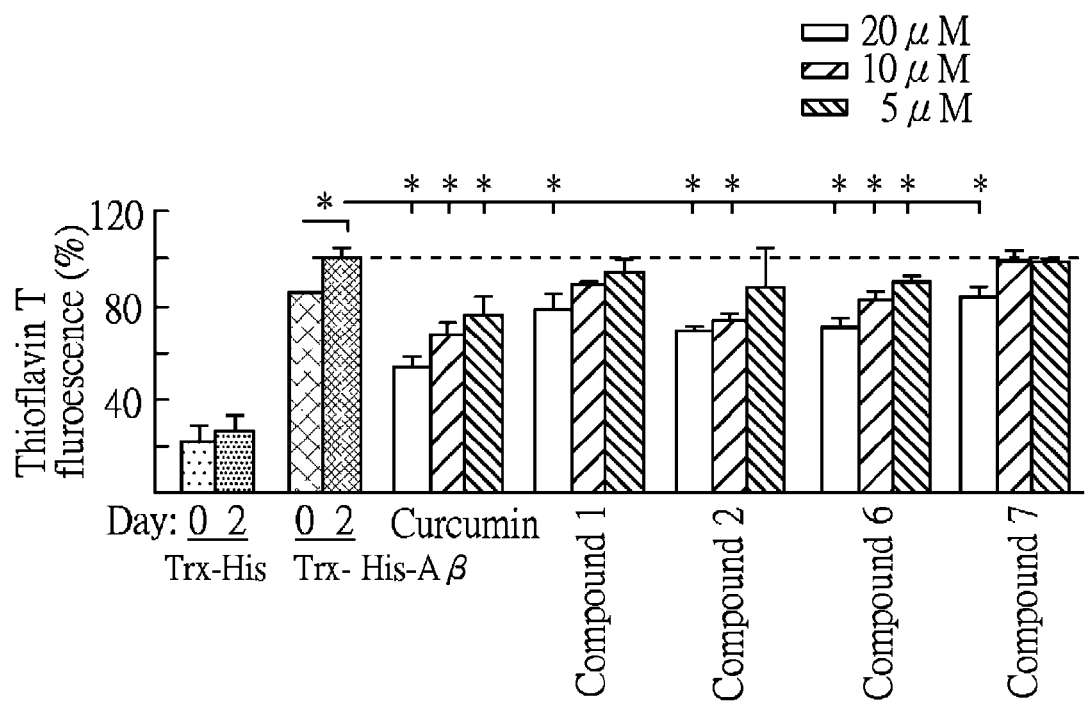
FIG. 2 shows quantitative result of Trx-His-Aβ biochemical assay after purified Trx-His-Aβ protein was treated with indolylquinoline derivatives and stained with thioflavin T in one preferred example of the present invention.

Aggregation of β-amyloid (Aβ) was considered as target for intervention. For the biochemical assay, the inventors overexpressed Trx-His tagged Aβ construct in *E. coli*. After metal-affinity chromatography purification, the misfolded Trx-His-Aβ proteins can be identified by thioflavin T staining assay. The fluorescent intensity is increased after thioflavin T binds misfolded Trx-His-Aβ protein, and thus the misfolding level of Trx-His-Aβ protein can be measured. The purified Trx-His-Aβ protein (10 µM) was incubated at 37° C. with the tested compounds 1-11 (5~20 µM) for 48 hr. Then thioflavin T (10 µM) was added for 5 min and fluorescence analyzed on a microplate reader (excitation: 420 nm, emission: 485 nm). The obtained quantitative result is shown in FIG. 2. To normalize, the relative thioflavin T fluorescence of Trx-His-Aβ protein with 2 days' incubation at 37° C. is set as 100%. *, $P<0.05$ (n=3).

When aggregate formation was measured with fluorescence generated by thioflavin T binding, significantly more Trx-His-Aβ aggregate formed after 2 days' incubation at 37° C. (100% vs. 85%, $P=0.009$), as shown in FIG. 2. As a positive control, curcumin in 5~20 µM significantly reduced the misfolded Aβ to 76~54% ($P=0.006$~<0.001). Significantly reduced Aβ aggregation was also observed with synthetic indolylquinoline compound 1 (79% in 20 µM, $P=0.010$), compound 2 (74~70% in 10~20 µM, $P=0.009$~0.011), compound 6 (90~71% in 5~20 µM, $P=0.006$~<0.001) and compound 7 (84% in 20 µM, $P=0.035$). In addition, Trx-His-Aβ protein aggregations were not significant decreased after treating with compounds 3-5 and 8-11 (not shown in the figure).

[Tet-On Aβ-GFP HEK-293 Cell Assay]

For cell assay, we used a HEK-293 cell clone (human embryonic kidney cells) with Tet-On Aβ-GFP expression as a screening platform. GFP fluorescence was used to reflect Aβ aggregation status as Aβ aggregated rapidly to cause the fused GFP misfolded. Inhibition of Aβ aggregation may improve GFP misfolding, leading to increasing fluorescence on Aβ-GFP expressing cells. Tet-On Aβ-GFP HEK-293 cells were pretreated with different concentrations of compounds 1, 2, 6, 7 and curcumin for 8 hr before inducing Aβ-GFP expression. Then doxycycline (Dox) (10 µM) was added to the medium for 64 hr to induce Aβ-GFP expression, and GFP fluorescence was assessed by a high-content analysis (HCA) system (ImageXpressMICRO, available from Molecular Devices).

Figure 3:
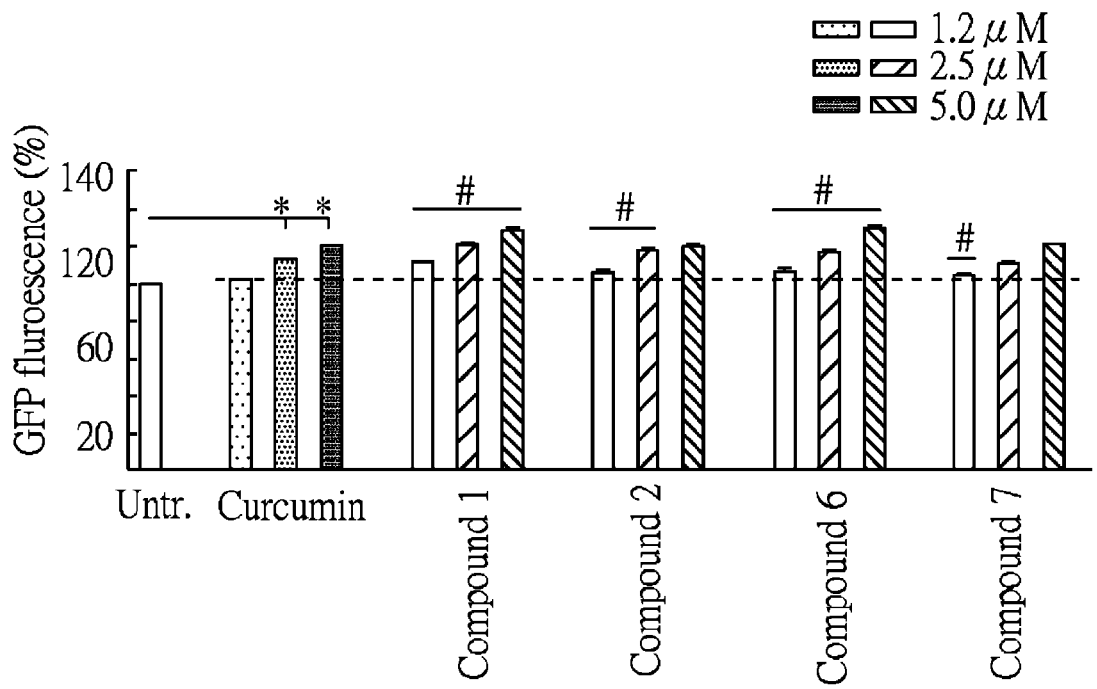
FIG. 3 shows quantitative result of GFP fluorescence in Tet-On Aβ-GFP HEK-293 cells treated with indolylquinoline derivatives in one preferred example of the present invention.

The quantitative result of GFP fluorescence in the present assay is shown in FIG. 3. To normalize, the relative GFP fluorescence of untreated cells (untreated with compounds 1, 2, 6 and 7, and curcumin) is set as 100%. *, $P<0.05$ as compared to the untreated cells; #, $P<0.05$ as compared to the same concentration curcumin-treated cells (n=3). As shown in FIG. 3, curcumin increased the Aβ-GFP fluorescence to 111~122% (2.5~5.0 µM, $P=0.003$~<0.001) as compared to untreated cells (100%). With above 80% of viable cells, significantly increased GFP fluorescence was observed with synthetic indolylquinoline compound 1 (112~129%), compound 6 (107~130%) (1.2~5.0 µM, $P=0.010$~<0.001), compound 2 (107~120%) (1.2~2.5 µM, $P=0.025$~0.002) and compound 7 (105%) (1.2 µM, $P<0.001$), as compared to the same concentration curcumin-treated cells.

Figure 4:
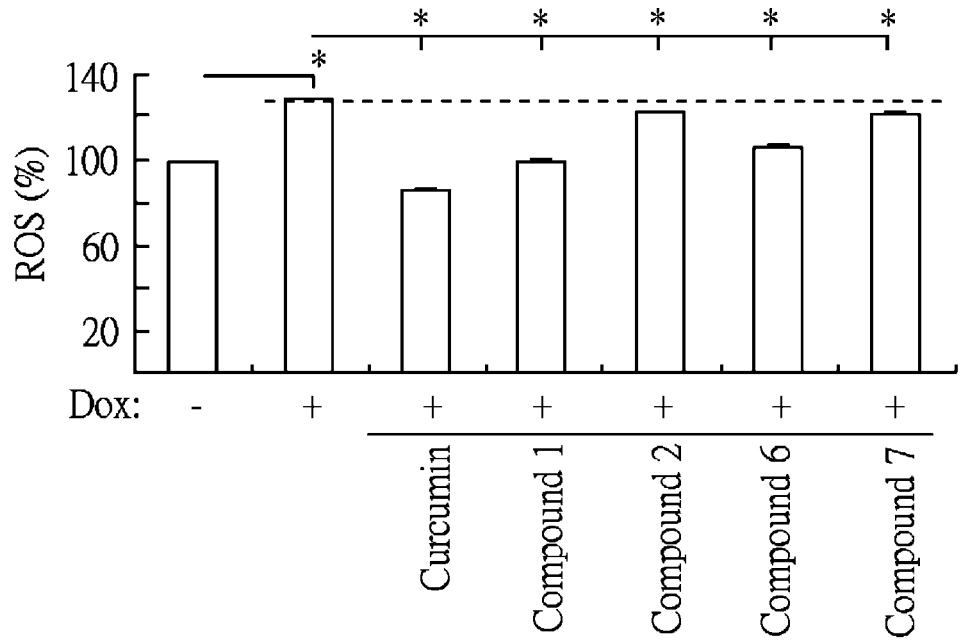
FIG. 4 shows quantitative result of ROS level in Tet-On Aβ-GFP HEK-293 cells treated with indolylquinoline derivatives in one preferred example of the present invention.

Given that Aβ deposition causes cell death via a number of potential mechanisms including oxidative stress, the inventor also performed ROS assay with curcumin or synthetic indolylquinoline compounds 1, 2, 6 and 7 treatment (5 µM). FIG. 4 shows the relative ROS level, wherein the relative ROS of uninduced cells is set as 100%. *, $P<0.05$ between induced vs. uninduced cells or compound-treated vs. untreated cells (n=3). Induced expression of Aβ-GFP significantly increased ROS level as compared to uninduced cells (128% vs. 100%, $P<0.001$). Treatment with curcumin significantly reduced ROS level as compared to the untreated cells (86% vs. 128%, $P<0.001$). Treatment with synthetic indolylquinoline compounds 1, 2, 6 and 7 (5 µM) significantly reduced ROS level induced by Aβ deposition (99~123% vs. 128%, $P=0.001$~<0.001).

[Tet-On Aβ-GFP SH-SY5Y Cell Assay]

Tet-On Aβ human neuroblastoma SH-SY5Y cells were used to examine the neuroprotective potential of the compounds of the present invention. Tet-On Aβ-GFP SH-SY5Y cells were plated into 24-well plates with 10 µM retinoic acid (RA), grown for 24 hr and treated with tested indolylquinoline compounds 1, 2, 6 and 7 (5 µM) for 8 hr. Then doxycycline (10 µM) was added to the medium to for 6 days. Neurite outgrowth was assessed after TUBB3 immunostaining, and examined with the HCA system. The result is shown in FIG. 5, wherein the relative neurite outgrowth of uninduced cells (untreated with Dox) is set as 100%. *, P<0.05 between induced vs. uninduced cells or compound-treated vs. untreated cells (n=3).

Figure 5:
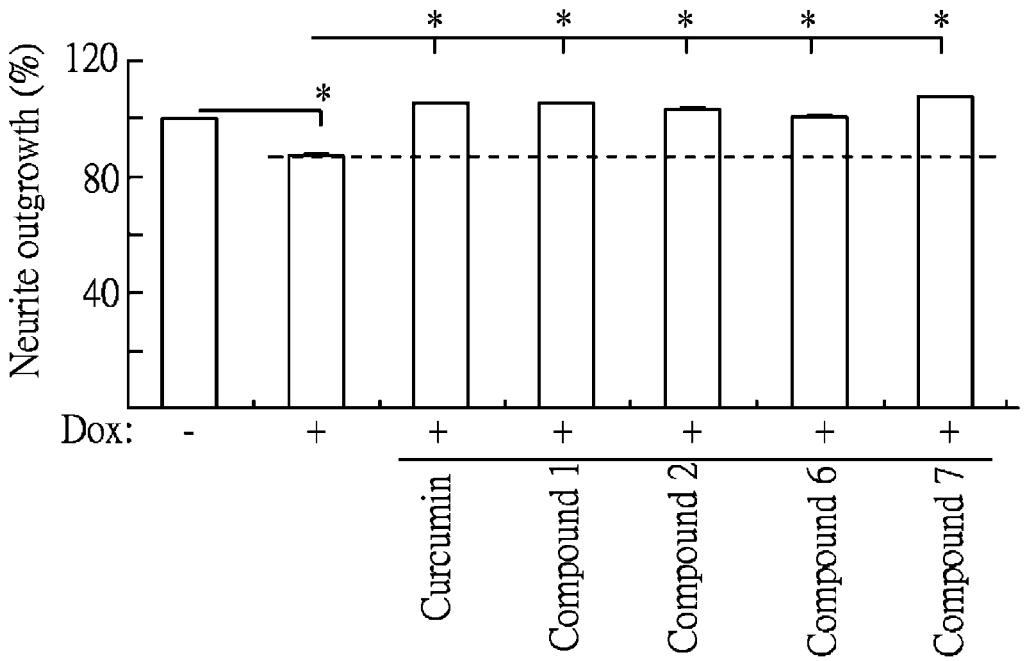
FIG. 5 shows quantitative result of neurite outgrowth of Tet-On Aβ SH-SY5Y cells treated with indolylquinoline derivatives in one preferred example of the present invention.

As shown in FIG. 5, induced expression of Aβ-GFP significantly reduced neurite outgrowth as compared to uninduced cells (87% vs. 100%, P<0.001). Treatment of curcumin significantly improved neurite outgrowth as compared to the untreated cells (untreated with compounds 1, 2, 6 and 7 and curcumin) (105% vs. 87%, P<0.001). Examination of neurite features of Aβ-GFP SH-SY5Y cells revealed that synthetic indolylquinoline compounds 1, 2, 6 and 7 (5 μM) significantly improved neurite outgrowth (101~108% vs. 87%, P<0.001).

To examine if the indolylquinoline compounds of the present invention up-regulated HSPB1 expression in Aβ-GFP SH-SY5Y cells, the Western blot analysis was performed to examine the expression level of HSPB1. The result is shown in FIG. 6, wherein the relative HSPB1 level of uninduced cells is set as 100%. *, P<0.05 between induced vs uninduced cells or compound-treated vs. untreated cells (n=3).

Figure 6:
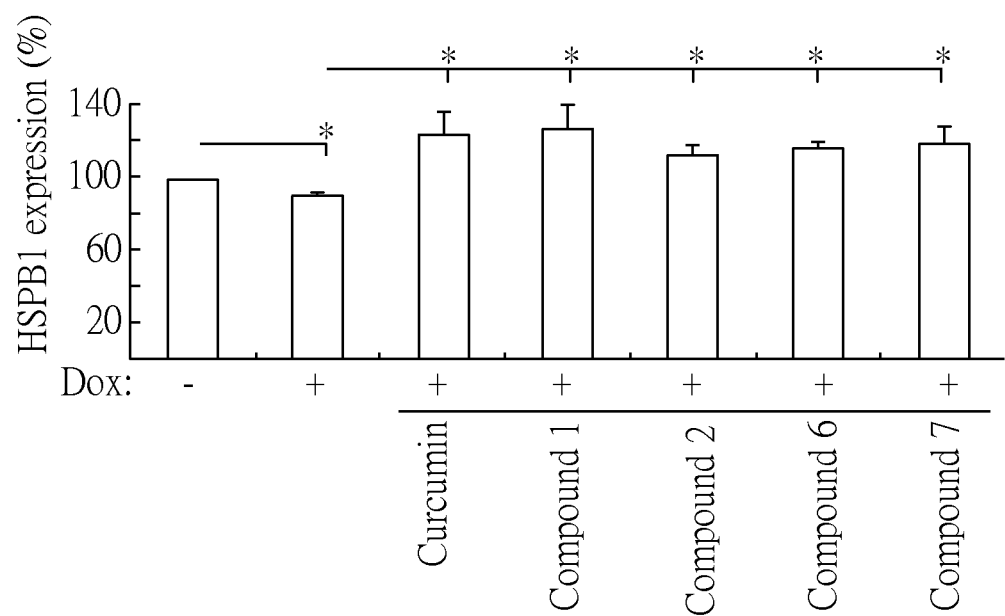
FIG. 6 shows quantitative result of HSPB1 expression in Aβ-GFP SH-SY5Y cells treated with indolylquinoline derivatives in one preferred example of the present invention.

As shown in FIG. 6, induced expression of Aβ-GFP attenuated the expression of HSPB1 as compared to uninduced cells (90% vs. 100%, P=0.006). Addition of curcumin, compounds 1, 2, 6 and 7 of the present invention (5 μM) led to significantly increased HSPB1 expression (curcumin: 123%; compound 1: 126%; compound 2: 112%; compound 6: 116%; and compound 7: 117%; P=0.044~0.001) as compared to untreated cells (90%).

[Mouse Hippocampal Primary Culture]

Figure 7:
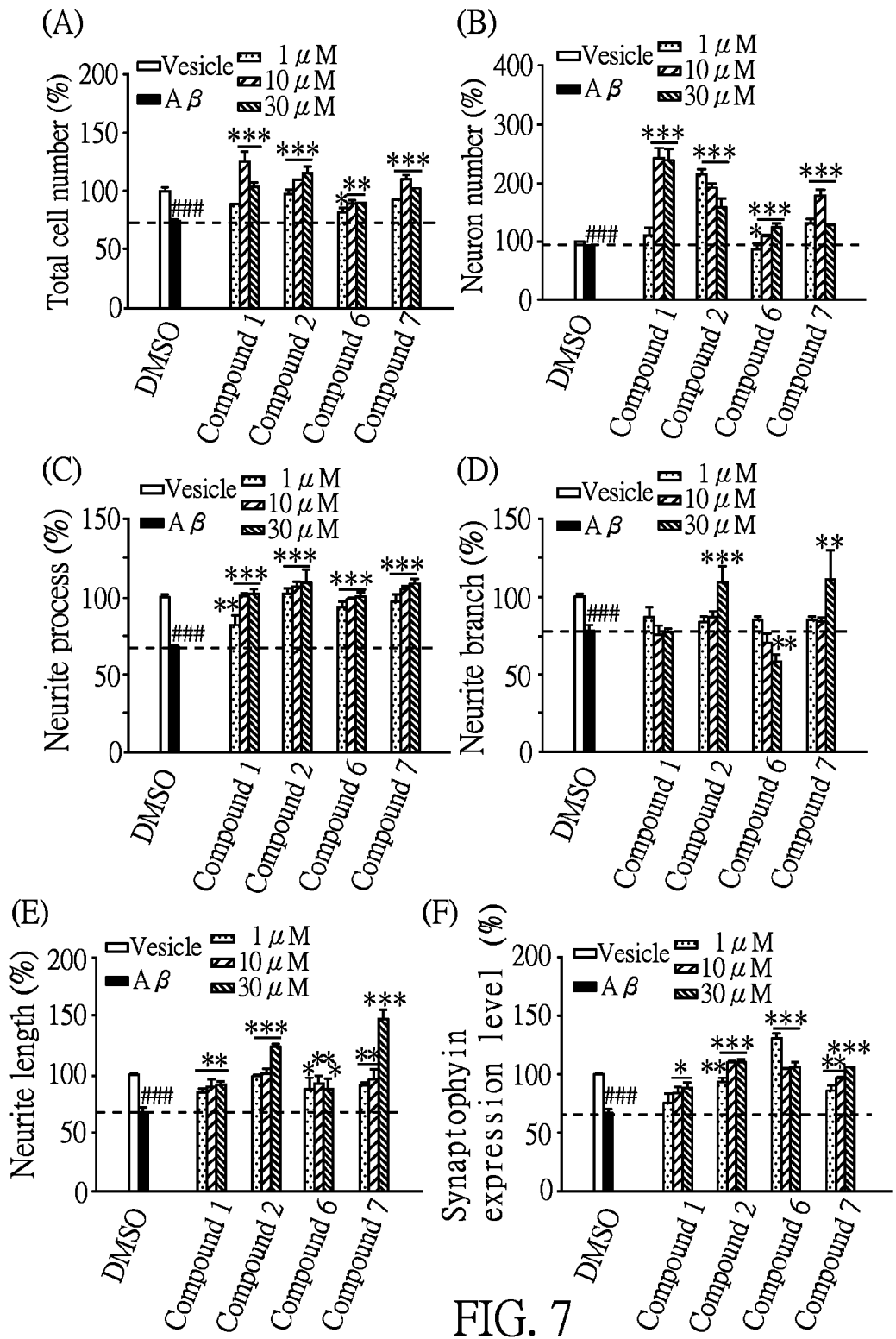
FIG. 7(A) to (F) respectively show quantitative results of total cell number, mature neuron number, neurite process, neurite branch, neurite length and synaptophysin expression level in Aβ-induced mouse hippocampal primary culture treated with indolylquinoline derivatives in one preferred example of the present invention.

Postnatal day 0-1 mouse hippocampus was isolated for primary culture, and used to confirm the neuroprotective potential of the compounds of the present invention. Oligomeric Aβ (1 μM) was applied to the primary culture after the indolylquinoline compound (compounds 1, 2, 6 and 7) administration (1, 10, or 30 μM) at day 9. Cells were harvested 1 hr later for immunocytochemical analysis and quantitated the total cell number (as shown in FIG. 7(A), by DAPI staining), mature neuron number (as shown in FIG. 7(B), by NeuN antibody staining), neurite process (as shown in FIG. 7(C), by MAP2 antibody staining), neurite branch (as shown in FIG. 7(D), by MAP2 antibody staining), neurite length (as shown in FIG. 7(E), by MAP2 antibody staining), and synaptophysin expression level (as shown in FIG. 7(F), by synaptophysin antibody staining) In FIG. 7(A) to (F), the relative amount of cells treated with vesicle (hexafluoroisopropanol) is set as 100%. ###, P<0.001 between cells treated with Aβ and vehicle (n=3). *, P<0.05; , P<0.01; *, P<0.001 between cells treated with Aβ combined the compound of the present invention and Aβ alone (n=3). Oligomeric Aβ significantly reduced total cells, mature neurons, neurite outgrowth and synaptophysin expression level as compared to vehicle-treated cells. Synthetic indolylquinoline compounds 1, 2, 6 and 7 (1, 10 or 30 μM) significantly improved total cells (FIG. 7(A)), mature neurons (FIG. 7(B)), neurite outgrowth (FIGS. 7(C)-(E)) and synaptophysin level (FIG. 7(F)) against the oligomeric Aβ toxicity in the hippocampal primary culture.

In the present invention, Trx-His-Aβ cell-free and Aβ-GFP 293/SH-SY5Y cell models with Aβ aggregation were used to screen synthetic indolylquinoline compounds potentially inhibiting Aβ aggregation. In Trx-His-Aβ biochemical assay, thioflavin T was used as a diagnostic of amyloid structure, as thioflavin T exhibiting enhanced fluorescence upon binding to amyloid fibrils. Among several tested synthetic indolylquinoline compounds (compounds 1-11 of the present invention), compounds 1, 2, 6 and 7 displayed good potential to inhibit Aβ aggregation. In Aβ-GFP cell assays, Tet-On HEK-293 cells with inducible Aβ-GFP expression were used as a cellular screening platform. Inhibitors that retard or block Aβ aggregation can be distinguished by increasing GFP fluorescence on Tet-On HEK-293 cells. Good aggregation-inhibitory effects were seen in Tet-On Aβ-GFP HEK-293 cells treated with tested synthetic indolylquinoline compounds 1, 2, 6 and 7, accompanying with reduced reactive oxygen species and enhanced HSPB1 chaperone expression. These tested compounds also promoted neurite outgrowth in Tet-On Aβ-GFP SH-SY5Y cells. The effect in promoting neuronal cell viability, neurite outgrowth, and synaptophysin expression level were also confirmed with mouse hippocampal primary culture under oligomeric Aβ-induced cytotoxicity. The results demonstrate how synthetic indolylquinoline compounds of the present invention are likely to work in Aβ-aggregation reduction, and provide insight into the possible working mechanism of indolylquinoline compounds in AD patients. These findings may have therapeutic applications in AD.

Although the present invention has been explained in relation to its preferred embodiment, it is to be understood that many other possible modifications and variations can be made without departing from the spirit and scope of the invention as hereinafter claimed.

What is claimed is:

1. A method for treating a disease associated with β-amyloid aggregation, comprising:

administering a pharmaceutical composition comprising a compound represented by the following formulas 2 to 4 to a subject in need thereof:

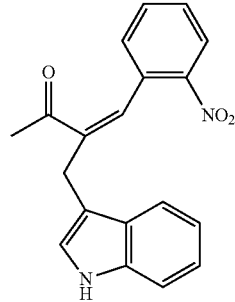

[Formula 2]

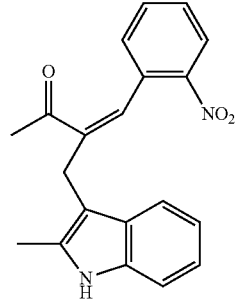

[Formula 3]

-continued

[Formula 4]

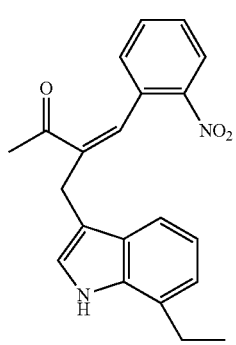

wherein the disease associated with β-amyloid aggregation is Alzheimer's disease.

2. The method as claimed in claim 1, wherein a concentration of the compound represented by the formulas 2 to 4 is in a range from 1 μM to 30 μM based on a total weight of the pharmaceutical composition.

3. The method as claimed in claim 1, wherein the pharmaceutical composition further comprises at least one pharmaceutically acceptable carrier, a diluent, or an excipient.

4. The method as claimed in claim 1, wherein the compound is encapsulated into liposome.

* * * * *